United States Patent
Yasuno et al.

(10) Patent No.: US 9,471,277 B2
(45) Date of Patent: Oct. 18, 2016

(54) PROGRAM FOR CORRECTING DATA MEASURED BY PS-OCT AND PS-OCT SYSTEM EQUIPPED WITH THE PROGRAM

(75) Inventors: Yoshiaki Yasuno, Tsukuba (JP); Lian Duan, Tsukuba (JP); Masahide Ito, Tsukuba (JP)

(73) Assignee: UNIVERSITY OF TSUKUBA, Tsukuba-Shi (JP)

( * ) Notice: Subject to any disclaimer, the term of this patent is extended or adjusted under 35 U.S.C. 154(b) by 329 days.

(21) Appl. No.: 14/122,228

(22) PCT Filed: Apr. 25, 2012

(86) PCT No.: PCT/JP2012/061064
§ 371 (c)(1),
(2), (4) Date: Dec. 17, 2013

(87) PCT Pub. No.: WO2013/008516
PCT Pub. Date: Jan. 17, 2013

(65) Prior Publication Data
US 2014/0115022 A1    Apr. 24, 2014

(30) Foreign Application Priority Data

Jul. 12, 2011  (JP) ................ 2011-153594

(51) Int. Cl.
*G01B 9/02*    (2006.01)
*G06F 7/483*   (2006.01)
(Continued)

(52) U.S. Cl.
CPC ............. *G06F 7/483* (2013.01); *A61B 5/0066* (2013.01); *A61B 5/7203* (2013.01); *G01B 9/0207* (2013.01); *G01B 9/02011* (2013.01); *G01B 9/02027* (2013.01); *G01B 9/02044* (2013.01);
(Continued)

(58) Field of Classification Search
CPC ............. G06F 17/10; G01B 9/02011; G01B 9/02012; G01B 9/02091
See application file for complete search history.

(56) References Cited

U.S. PATENT DOCUMENTS 6,377,349 B1    4/2002  Fercher
7,557,929 B2 *  7/2009  Fang-Yen .......... G01B 9/02072
                                              356/484

(Continued)

FOREIGN PATENT DOCUMENTS

JP    H11-325849 A    11/1999
JP    2002-310897 A   10/2002

(Continued)

OTHER PUBLICATIONS

International Search Report (ISR) mailed May 22, 2012, issued for International application No. PCT/JP2012/061064.

*Primary Examiner* — Chuong D Ngo
(74) *Attorney, Agent, or Firm* — Law Office of Katsuhiro Arai

(57) ABSTRACT

Data measured by PS-OCT is corrected in a non-linear manner to enhance the quantitative analysis capability of PS-OCT and permit accurate quantitative diagnosis, including diagnosis of disease stage of lesions, as a useful means for computer diagnosis. Even when retardation per PS-OCT 1 contains error and becomes noise and its distribution is not normal or symmetrical around the true value, measured data is converted using a distribution conversion function obtained by analyzing the characteristics of noise via Monte Carlo simulation to remove the systematic error and estimate the true value otherwise buried in noise and thereby correct the PS-OCT 1 image more clearly.

8 Claims, 7 Drawing Sheets

(51) Int. Cl.
*A61B 5/00* (2006.01)
*G01N 21/27* (2006.01)
*G01N 21/47* (2006.01)
*A61B 3/10* (2006.01)

(52) U.S. Cl.
CPC ....... *G01B 9/02088* (2013.01); *G01B 9/02091* (2013.01); *A61B 3/102* (2013.01); *G01B 2290/45* (2013.01); *G01B 2290/70* (2013.01); *G01N 21/274* (2013.01); *G01N 21/4795* (2013.01)

(56) References Cited

U.S. PATENT DOCUMENTS

| | | | | |
|---|---|---|---|---|
| 7,643,153 B2 * | 1/2010 | de Boer | ............... | A61B 5/0059 356/479 |
| 7,978,338 B2 * | 7/2011 | De Groot | ........... | G01B 11/2441 356/497 |
| 8,018,598 B2 * | 9/2011 | Cense | .................... | A61B 3/102 356/456 |
| 2011/0170111 A1 * | 7/2011 | Rolland | ................. | G01B 9/021 356/479 |
| 2012/0120408 A1 | 5/2012 | Yasuno et al. | | |

FOREIGN PATENT DOCUMENTS

| | | |
|---|---|---|
| JP | 2004-028970 A | 1/2004 |
| JP | 2008-175698 A | 7/2008 |
| JP | 2009-031229 A | 2/2009 |
| WO | 2010/143601 A1 | 12/2010 |

\* cited by examiner

PROGRAM FOR CORRECTING DATA MEASURED BY PS-OCT AND PS-OCT SYSTEM EQUIPPED WITH THE PROGRAM

This application is the U.S. National Phase under 35 U.S.C. §371 of International Application PCT/JP2012/061064, filed Apr. 25, 2012, which claims priorities to Japanese Patent Applications No. 2011-153594, filed Jul. 12, 2011. The International Application was published under PCT Article 21(2) in a language other than English.

TECHNICAL FIELD

The present invention relates to a program that corrects data measured by optical coherence tomography (OCT) to achieve higher accuracy, as well as an OCT system installed with the program.

In particular, the present invention relates to a program that corrects data measured with a polarization-sensitive optical coherence tomography device (such device is also called polarization-sensitive optical image measuring device, polarization-sensitive OCT or polarization optical interferometer tomography device, but hereinafter referred to as "PS-OCT" as it is normally called) to achieve higher accuracy, as well as a PS-OCT system installed with the program.

BACKGROUND ART

Traditionally OCT has been used to capture information regarding the interior of an object, or specifically its differential structure based on back scattering, reflectance distribution and refractive index distribution, in a non-destructive manner at high resolution.

One non-destructive tomographic measurement technology used in the medical field, etc., is optical coherence tomography (OCT) (refer to Patent Literature 1). OCT uses light as a measuring probe and therefore provides the benefit of allowing for measurement of reflectance distribution, refractive index distribution, spectroscopic information, polarization information (double refractive index distribution), etc., of the measuring target.

Basic OCT 43 uses the Michelson interferometer whose operating principles are explained using FIG. 8. The light emitted from a light source 44 is parallelized by a collimating lens 45 and then split into reference light and object light by a beam splitter 46. The object light is focused onto a measuring target 48 by an objective lens 47 in the object arm, and the scattered/reflected light returns to the objective lens 47 and beam splitter 46.

On the other hand, the reference light passes through an objective lens 49 in the reference arm and then reflects on a reference mirror 50, travels through the objective lens 49 again, and returns to the beam splitter 46. The object light and reference light thus returning to the beam splitter 46 enter a condensing lens 51 and get focused onto an optical detector 52 (photodiode, etc.).

For the OCT light source 44, a light source capable of generating light of low temporal coherence (interference between lights emitted by the light source at different times is kept to a minimum) is used. With the Michelson interferometer using a light source of low temporal coherence light, interference signals manifest only when the distance from the reference arm is roughly equivalent to the distance from the object arm. This means that, when the intensity of interference signal is measured with the optical detector 52 while changing the differential optical path length ($\tau$) between the reference arm and object arm, interference signals at varying differential optical path lengths (interferogram) can be obtained.

The shape of this interferogram represents the reflectance distribution of the measuring target 48 in the depth direction, and a one-dimensional scan of the interferogram in the axial direction reveals the structure of the measuring target 48 in the depth direction. With OCT 43, therefore, the structure of the measuring target 48 in the depth direction can be measured by optical path length scanning.

A two-dimensional scan combining the aforementioned scan in the axial direction (direction A) with a mechanical scan (scan B) in the lateral direction (direction B) gives a two-dimensional section image of the measuring target. A scanner that performs this lateral scan may be configured in such a way that the measuring target is moved directly, or it may be configured in such a way that the target is fixed and the objective lens is shifted, or it may be configured in such a way that both the measuring target and objective lens are fixed and the galvano-mirror near the pupil plane of the objective lens is turned to change its angle, or the like.

Advanced versions of the basic OCT mentioned above include swept source OCT (SS-OCT) where the wavelengths of the light source are scanned to obtain spectral interference signals, and spectral domain OCT where a spectroscope is used to obtain spectral signals. The latter includes Fourier domain OCT (FD-OCT; refer to Patent Literature 2) and PS-OCT (refer to Patent Literature 3).

In swept source OCT, a high-speed wavelength scanning laser is used to change the wavelength of the light source, after which spectral signals and synchronously acquired light source scanning signals are used to rearrange the interference signals, which are then processed to obtain a three-dimensional optical tomographic image. Swept source OCT can also use a monochrometer as the means for changing the wavelength of the light source.

Fourier domain OCT is characterized in that a wavelength spectrum of the reflected light from the measuring target is acquired by a spectrometer, and this spectral intensity distribution is Fourier-converted to retrieve signals in real space (OCT signal space), and therefore Fourier domain OCT does not require scanning in the depth direction, but scanning in the X-axis direction permits measurement of the section structure of the measuring target.

PS-OCT provides an optical coherence tomography device that continuously modulates the polarized state of the linearly polarized beam simultaneously during scan B, to capture the polarization information of the sample (measuring target) and thereby permit measurement of the more detailed structure and anisotropy of refractive index of the sample.

To be more specific, PS-OCT acquires a wavelength spectrum of the reflected light from the measuring target using a spectrometer, just like Fourier domain OCT, but is different in that the incident light and reference light are horizontally and linearly polarized, vertically and linearly polarized, linearly polarized at 45°, and circularly polarized through a ½ wavelength plate, ¼ wavelength plate, etc., respectively, after which the reflected light from the measuring target and the reference light are superimposed with each other and the superimposed light is passed through a ½ wavelength plate, ¼ wavelength plate, etc., to, for example, allow only the horizontally polarized component to enter the spectrometer to cause interference, thereby retrieving and Fourier-converting the component associated with the specific polarized state of object light. This PS-OCT does not require scanning in the depth direction, either.

PRIOR ART LITERATURES

Patent Literatures

Patent Literature 1: Japanese Patent Laid-open No. 2002-310897
Patent Literature 2: Japanese Patent Laid-open No. Hei 11-325849
Patent Literature 3: Japanese Patent Laid-open No. 2004-028970

SUMMARY OF THE INVENTION

Problems to be Solved by the Invention

Generally when application of OCT to bioinstrumentation is considered, the differential structure of the refractive index distribution of an object can be captured in a non-destructive manner at high resolution; however, a drop in resolution makes structural capture no longer possible in the case of measurement of a biological sample having polarization dependence due to double refraction caused by a fibrous structure (extending direction of the fiber, etc.) or difference in tooth enamel structure.

In this sense, PS-OCT causes the scattering light component from a specific part to interfere with the reference light in a polarized state so that the resulting interference component reflects the polarization characteristics strongly and therefore phase retardation information (retardation amount) can be obtained, as result of which the polarization information and double refraction information of a specific part of a cross section in the depth direction can be captured. Accordingly, PS-OCT provides a useful examination device in the clinical fields where broad, non-invasive tissue discrimination is required, such as ophthalmology, circulatory medicine, respiratory medicine and digestive medicine, among others.

As mentioned above, PS-OCT is useful in the qualitative observation of tissue contrast in that it provides an optical tomography device that visualizes the polarization characteristics of tissues in a non-invasive manner. However, the inventors of the present invention found, during the course of earnest research and development for the purpose of increasing the accuracy of PS-OCT, that PS-OCT does not necessarily offer sufficient accuracy in the observation of lesions for quantitative observation with the aim of accurate classification of disease stage, etc., and thus has room for further improvement.

The present invention is intended to provide a solution to address the need for improvement presented by the traditional PS-OCT above, and the object of the present invention is to realize a program that allows for accurate quantitative diagnosis of disease stage, etc., by correcting PS-OCT measured data in a non-linear manner and enhancing the quantitative analysis capability of PS-OCT, as well as a PS-OCT system installed with the program.

To be more specific, PS-OCT-measured retardation (amount of phase delay or amount of phase difference) contains error and is distributed around the true value (this is referred to as retardation distribution or phase difference distribution). Generally this distribution is not symmetrical and may be asymmetrical with the true value not necessarily at the center. Accordingly, the correct retardation cannot be obtained from any standard phase analysis where the average is taken.

The present invention aims to solve this conventional problem of PS-OCT and the object of the present invention is to realize a program that, even when retardation contains error and becomes noise and its distribution is not normal or symmetrical around the true value, converts measured data using a distribution conversion function obtained by analyzing the characteristics of noise via Monte Carlo simulation to remove the systematic error and estimate the true value otherwise buried in noise and thereby correct the PS-OCT image more clearly, as well as PS-OCT system installed with this program.

Means for Solving the Problems

To achieve the aforementioned objects, the present invention provides a program to be installed in a computer for processing measured data obtained by PS-OCT, where such program is characterized in that it causes the computer to function as a means for obtaining the true phase constant by using a non-linear conversion function to convert phase difference distribution data on retardation measured by PS-OCT to symmetrical phase difference distribution data and then averaging the data.

To achieve the aforementioned objects, the present invention provides a program to be installed in a computer for processing measured data obtained by PS-OCT, wherein such program is characterized in that it causes the computer to function as: a means for creating and storing multiple sets of phase difference distribution data for different ESNRs beforehand, where each set comprises a distribution corresponding to each of the multiple phase constants from 0 to $\pi$; a means for determining the coefficient of non-linear conversion function for converting phase difference distribution data measured by PS-OCT to symmetrical phase difference distribution data; a means for estimating the ESNR from phase difference distribution data measured by PS-OCT and then using the estimated ESNR to select one of the multiple sets of phase difference distributions created for different ESNRs; a means for converting phase difference distribution data measured by PS-OCT to symmetrical phase difference distribution data, by using the conversion function based on the coefficient determined according to the selected set of phase difference distribution; and a means for obtaining the true phase constant by averaging the symmetrical phase difference distribution data.

To achieve the aforementioned objects, the present invention provides a PS-OCT system equipped with PS-OCT and a computer for processing measured data obtained by the PS-OCT, wherein such PS-OCT system is characterized in that the computer is equipped with an input device, output device, CPU, and storage device, and functions as a means for obtaining the true phase constant by using a non-linear conversion function to convert phase difference distribution data measured by PS-OCT to symmetrical phase difference distribution data and then averaging the data.

To achieve the aforementioned objects, the present invention provides a PS-OCT system equipped with PS-OCT and a computer for processing measured data obtained by the PS-OCT, wherein such PS-OCT system is characterized in that the computer has an input device, output device, CPU, and storage device and functions as: a means for creating and storing multiple sets of phase difference distribution data for different ESNRs beforehand, where each set comprises a distribution corresponding to each of the multiple phase constants from 0 to $\pi$; a means for determining the coefficient of non-linear conversion function for converting phase difference distribution data measured by PS-OCT to symmetrical phase difference distribution data; a means for estimating the ESNR from phase difference distribution data measured by PS-OCT and then using the estimated ESNR to select one of the multiple sets of phase difference distributions created for different ESNRs; a means for converting phase difference distribution data measured by PS-OCT to symmetrical phase difference distribution data, by using the conversion function based on the coefficient determined according to the selected set of phase difference distribution; and a means for obtaining the true phase constant by averaging the symmetrical phase difference distribution data.

The non-linear conversion function conforms to Equation (2) presented later.

The means for determining a coefficient of conversion function comprises changing the non-linear conversion function from 0 to $\pi$ in steps of $\pi/m$ to create Equation (3) presented later that is an m+1 number of simultaneous equations as mentioned later and then solving the simultaneous equations to create a table of coefficient of conversion function bi. Note that m represents the number of times $\pi$ is divided.

The means for solving the simultaneous equations to determine the coefficient of conversion function may comprise numerically obtaining a pseudo-inverse matrix DM+ of matrix DM per Equation (4) presented later and then calculating Equation (5) presented later to uniquely determine an optimal coefficient of conversion function bi.

The means for determining the coefficient of conversion function may comprise using the calculus of variation to uniquely determine an optimal coefficient of conversion function bi in such a way as to minimize the square error indicated by Equation (6) presented later.

Effects of the Invention

According to the present invention, data measured by PS-OCT can be corrected in a non-linear manner to enhance the quantitative analysis capability of PS-OCT, and accordingly the PS-OCT system proposed by the present invention permits accurate quantitative diagnosis, including diagnosis of disease stage of lesions, and thus can be utilized as a useful means for computer diagnosis, unlike with the conventional PS-OCT whose use was limited to morphological observation, etc., of lesions.

MODE FOR CARRYING OUT THE INVENTION

Figure 1:
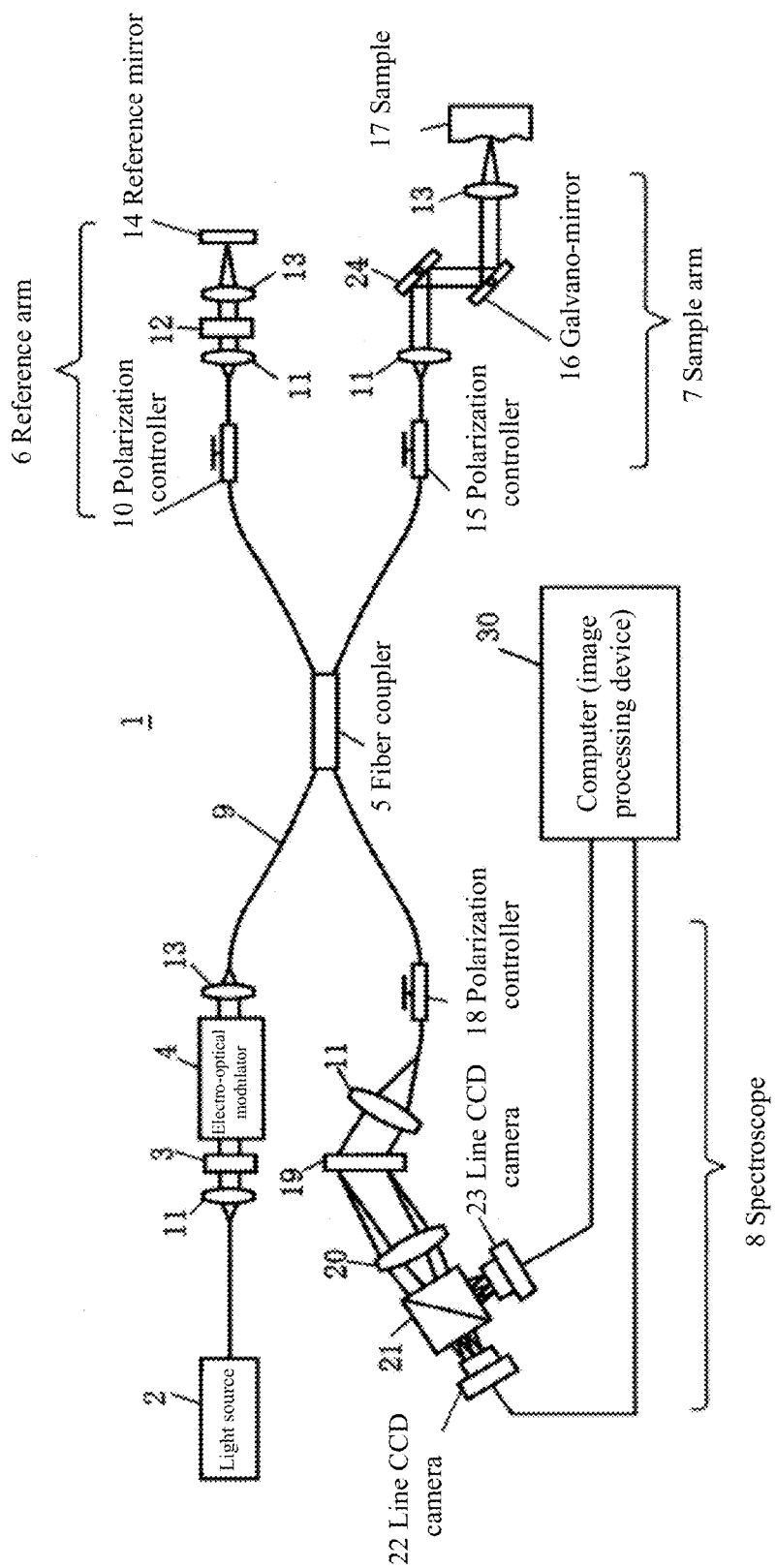
FIG. 1 is a diagram showing the overall configuration of the PS-OCT system proposed by the present invention

A mode for carrying out the program for correcting PS-OCT-measured data, as well as PS-OCT system installed with the program, as proposed by the present invention, is explained below by referring to the drawings.

The PS-OCT system proposed by the present invention has PS-OCT and an image processing device for processing image data obtained by PS-OCT. A standard computer is used for the image processing device, and the program proposed by the present invention causes it to function as a means for correcting image data obtained by PS-OCT.

(PS-OCT)

PS-OCT is already disclosed in Japanese Patent No. 4344829, etc., but an overview is presented since it is the background technology of the present invention.

The polarization-sensitive optical coherence tomography device proposed by the present invention uses an EO modulator (polarization modulator or electro-optical modulator) to continuously modulate the polarized beam (beam linearly polarized by the polarizer) from the light source simultaneously during (synchronously with) scan B, and splits the continuously polarization-modulated polarized beam, with one part scanned as incident beam and irradiated onto the sample to obtain the reflected light (object light), and the other part used as reference light, thereby causing a spectral interference of the two to perform OCT measurement.

Then, the system configuration is characterized in that, of the components of this spectral interference, the vertically polarized component (V) and horizontally polarized component (H) are measured simultaneously using two optical detectors to obtain the Jones vector (H image and V image) representing the polarization characteristics of the sample.

FIG. 1 is a diagram showing the overall configuration of the optical system of the polarization-sensitive optical coherence tomography device proposed by the present invention. A polarization-sensitive optical coherence tomography device 1 shown in FIG. 1 is equipped with optical elements such as a light source 2, polarizer 3, EO modulator 4, fiber coupler (optical coupler) 5, reference arm 6, sample arm 7, and spectroscope 8. Although the optical elements constituting the optical system of this polarization-sensitive optical coherence tomography device 1 are connected by fibers 9, a structure of non-fiber connection type (free space type) is also permitted.

For the light source 2, a super luminescent diode (SLD) having a broadband spectrum is used. The light source 2 may be a pulse laser. A collimating lens 11, polarizer 3 that linearly polarizes the light from the light source 2, EO modulator (polarization modulator or electro-optical modulator) 4 whose phase advance axis is set in the 45° direction, condensing lens 13, and fiber coupler 5, are connected to the light source 2 in this order.

The EO modulator 4 continuously changes the phase difference (retardation) between the phase advance axis and the phase delay axis orthogonal thereto, by fixing the phase advance axis in the 45° direction and sinusoidally modulating the voltage applied to the EO modulator 4, and when the resulting light that was output from the light source 2 and (vertically and) linearly polarized by the polarizer 3 enters the EO modulator 4, the light is modulated according to the above modulation cycle in the sequence of linear polarization→elliptical polarization→linear polarization, and so on. For the EO modulator 4, any commercially available EO modulator can be used.

Connected to the fiber coupler 5 via branching fibers 9 are the reference arm 6 and sample arm 7. The reference arm 6 has a polarization controller 10, collimating lens 11, polarizer 12, condensing lens 13 and reference mirror (fixed mirror) 14, in this order. The polarizer 12 on the reference arm 6 is used to select a direction that prevents the intensity of the light returning from the reference arm 6 from changing even when the polarized state is modulated as mentioned above. The direction (polarization direction of linear polarization) of this polarizer 12 is adjusted together with the polarization controller 10.

The sample arm 7 has a polarization controller 15, collimating lens 11, fixed mirror 24, galvano-mirror 16 and condensing lens 13, in this order, and the incident beam from the fiber coupler 5 is scanned by the 2-axis galvano-mirror 16 and irradiated onto a sample 17. The reflected light from the sample 17 returns to the fiber coupler 5 again as object light and is superimposed with the reference light to become the interference beam to be sent to the spectroscope 8.

The spectroscope 8 is equipped with a polarization controller 18, collimating lens 11, (polarization-sensitive volume phase holographic) diffraction lattice 19, Fourier conversion lens 20, polarization beam splitter 21 and two optical detectors 22, 23, connected in this order. In this embodiment, line CCD cameras (one-dimensional CCD cameras) are used for the optical detectors 22, 23. The interference beam sent from the fiber coupler 5 is collimated by the collimating lens 11 and spectrally split into interference spectrum by the diffraction lattice 19.

The interference spectrum beam spectrally split by the diffraction lattice 19 is Fourier-converted by the Fourier conversion lens 20 and split into the horizontal component and vertical component by the polarization beam splitter 21, and detected by the two line CCD cameras (optical detectors) 22, 23, respectively. These two line CCD cameras 22, 23 are used to detect the phase information of both the horizontal polarization signal and vertical polarization signal, so the two line CCD cameras 22, 23 must contribute to the formation of the same spectroscope.

It should be noted that the light source 2, reference arm 6, sample arm 7 and spectroscope 8 have their own polarization controllers 10, 15, 18, which are used to adjust the initial polarized state of each of the beams sent to the reference arm 6, sample arm 7 and spectroscope 8 from the light source 2, so as to control the polarized state, based on continuous modulation by the EO modulator 4, in order to maintain a relationship between the reference light and object light characterized by a fixed amplitude and fixed relative polarized state and also maintain a fixed amplitude and fixed relative polarized state at the spectroscope 8 connected to the fiber coupler 5.

In addition, the EO modulator 4 is stopped when calibrating the spectroscope 8 containing the two line CCD cameras 22, 23. The reference light is blocked and a slide glass and reflective mirror are put on the sample arm 7. This arrangement assures that the horizontal polarization component and vertical polarization component will have the same peak position. Then, the OCT signals from the surface behind the slide glass and from the reflective mirror are detected by the two spectroscopes 8. The peak phase difference of the OCT signals is monitored.

This phase difference should be zero at all depths in the optical axis direction. Next, the signals are windowed and reverse-Fourier-converted in order to obtain a complex spectrum at the spectroscope 8 containing the two line CCD cameras 22, 23. Since this phase difference should be zero at all frequencies, these values are monitored to align the physical positions of the two line CCD cameras 22, 23 to minimize the phase difference.

Operating Principles of PS-OCT:

The characteristics of the present invention are as follows. The light from the light source 2 is linearly polarized and the linearly polarized beam is passed through the EO modulator 4 for continuous modulation of the polarized state. In other words, the EO modulator 4 continuously changes the phase difference (polarization angle: retardation) between the phase advance axis and phase delay axis orthogonal thereto, by fixing the phase advance axis in the 45° direction and sinusoidally modulating the voltage applied to the EO modulator 4, and when the resulting light that was output from the light source 2 and (vertically and) linearly polarized by the linear polarizer enters the EO modulator 4, the light is modulated according to the above modulation cycle in the sequence of linear polarization→elliptical polarization→linear polarization, and so on.

Scan B is then synchronously performed simultaneously with the continuous modulation by the EO modulator 4 of the polarized state of the linearly polarized beam. To be specific, several cycles of continuous modulation of polarization by the EO modulator 4 are performed during one scan B. Here, one cycle refers to the period during which the polarization angle (retardation) Ø changes from 0 to $2\pi$. In essence, during this one cycle the polarization of light from the polarizer is modulated continuously in the sequence of linear polarization (vertical polarization)→elliptical polarization→linear polarization (horizontal polarization), and so on.

At the same time as this continuous modulation of the polarization of the polarized beam, the sample arm 7 performs scan B by scanning the incident beam over the sample 17 using the galvano-mirror 16, and the interference spectrum of the resulting reflected light, or object light, and the reference light, is detected at the spectroscope 8, by the two line CCD cameras 22, 23, in the form of its horizontal polarization component and vertical polarization component. This way, two scan A-B images corresponding to the horizontal polarization component and vertical polarization component are obtained by a single scan B.

As mentioned above, multiple cycles of continuous modulation of the polarization of the polarized beam are performed during a single scan B, where the polarization information of the horizontal polarization component and vertical polarization component detected by the two line CCD cameras 22, 23 during each cycle (one cycle) of continuous modulation provides the polarization information of one pixel. The two line CCD cameras 22, 23 synchronize the polarization information with the detection timing signals during one cycle of continuous modulation, with the appropriate number of detections (number of imports) per cycle determined as deemed appropriate, such as four times, eight times, and so on.

The data of the two scan A-B images thus obtained during one scan B is Fourier-converted one-dimensionally in the direction of scan B. This gives the zeroth, first and negative first peaks. Now, when the zeroth peak is extracted from each data set and reverse Fourier conversion is performed using the extracted data alone, images H0 and V0 are obtained. Similarly, extracting the first peak from each data set and performing reverse Fourier conversion using the extracted data alone gives images H1 and V1.

From images H0 and H1, J (1,1) and J (1,2) can be obtained from among the Jones matrix components indicating the polarization characteristics of the sample 17. Then, from images V0 and V1, J (2,1) and J (2,2) can be obtained from among the Jones matrix components indicating the polarization characteristics of the sample 17.

It should be noted that the Jones matrix components J (1,1), J (1,2), J (2,1) and J (2,2) mentioned here according to the description of Patent Literature 1 correspond to the Jones matrix components $I_{0H}(z)$, $I_{1H}(z)$, $I_{0V}(z)$ and $I_{1V}(z)$ in Equation (1) presented later in connection with the present invention.

Information containing four polarization characteristics is thus obtained by one scan B. Then, when Fourier conversion is performed on the four information pieces in the direction of scan A in the same manner as under normal FD-OCT, measured data of four A-B images, each containing the depth direction information of the sample 17 as represented by the first peak and each corresponding to the applicable polarization characteristics, is obtained.

(Program and PS-OCT System Proposed by the Present Invention)

Figure 2:
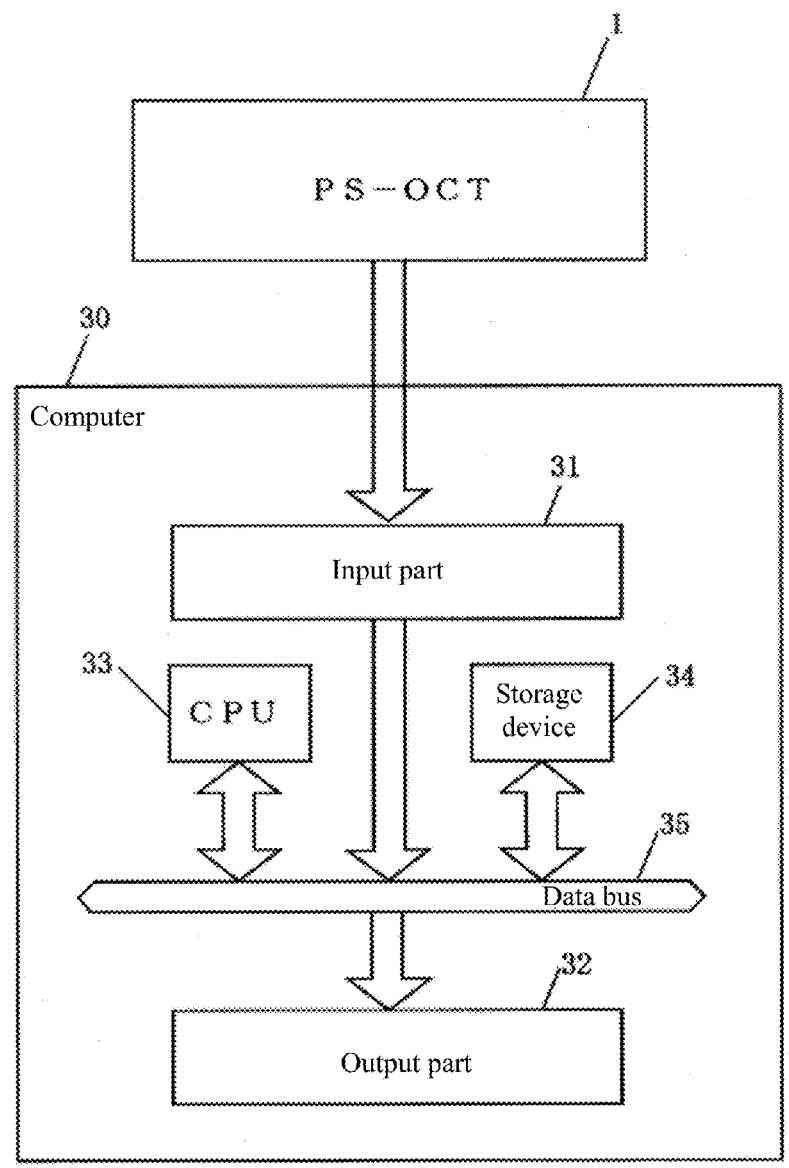
FIG. 2 is a diagram showing an image processing computer of the PS-OCT system proposed by the present invention

The measured data obtained according to the PS-OCT configuration above is input to a computer 30 used as an image processing device. This computer 30 is a standard computer and has an input part 31, output part 32, CPU 33, storage device 34, and data bus 35, as shown in FIG. 2.

The program installed in the PS-OCT system proposed by the present invention is the program stored in the storage device 34 of the computer 30, where this program causes the computer 30 to function as a means for correcting the measured data of images obtained by PS-OCT and input to the computer 30 for clearer correction of PS-OCT images. As this program is installed, the PS-OCT system proposed by the present invention becomes a system equipped with a means for correcting images more clearly.

In other words, conventionally, images obtained from raw data (raw polarization phase delay data) measured by PS-OCT were used directly for diagnosis and various other applications. With the program and PS-OCT system proposed by the present invention, on the other hand, raw data measured by PS-OCT can be corrected using a non-linear function for highly accurate biological double diffraction measurement, where this non-linear function is designed beforehand by performing a simulation on the computer 30 according to the Monte Carlo analysis method using the program proposed by the present invention.

The following explains in detail the program and PS-OCT system installed with the program proposed by the present invention.

Figure 3:
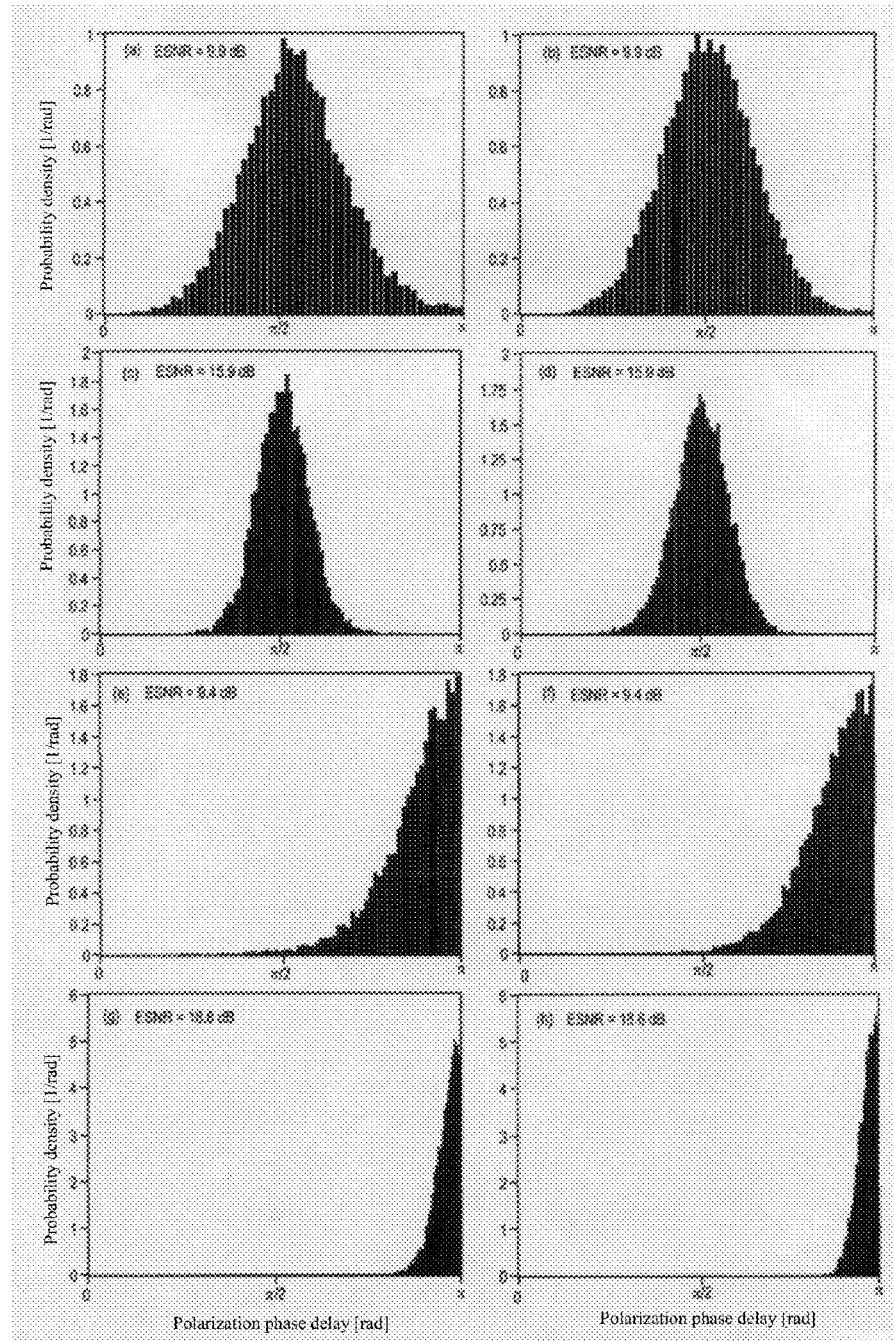
FIG. 3 shows retardation (phase difference, phase delay amount) distribution maps (phase difference distribution maps), where the four maps on the right side provide distribution maps of phase differences measured by PS-OCT, while those on the left side provide distribution maps of phase differences created by simulation.

FIG. 3 shows retardation (phase difference, phase delay amount) distribution maps (phase difference distribution maps). The horizontal axis represents phase, while the vertical axis represents retardation frequency. Phase difference distributions based on PS-OCT measured retardations are shown on the right side of FIG. 3, while phase difference distributions created by simulation are shown on the left side of FIG. 3.

Multiple sets of phase difference distributions are created by changing the ESNR, where one set comprises a m+1 number of data dividing the horizontal axis by $\pi/m$ (m+1 number of phase difference distributions). For example, multiple sets are created by changing the ESNR, where one set comprises 61 data sets dividing the horizontal axis by $\pi/60$ where m=60.

In FIG. 3, phase difference distributions of two different ESNR sets taken at $\pi/2$ and $\pi$ are shown.

A noise model of PS-OCT retardation is expressed by Equation (1) below by setting an additive noise to each element of the Jones matrix. Here, S indicates the true retardation value, N indicates noise, and I indicates the measured value. The subscripts 0, 1 represent measurement channels (refer to the optical detectors 22, 23 in FIG. 1). Each of the Jones matrix components explained in Paragraph 0052 above corresponds to the measured value I being a sum of the true value S and noise N. Here, z represents the coordinate in the depth direction and each element of the Jones matrix corresponds to the integral amount of retardations, etc., from the surface (z=0) to depth z.

[Number 1]

$$\begin{bmatrix} I_{0,H}(z) & I_{1,H}(z) \\ I_{0,V}(z) & I_{1,V}(z) \end{bmatrix} = \begin{bmatrix} S_{0,H}(z) & S_{1,H}(z) \\ S_{0,V}(z) & S_{1,V}(z) \end{bmatrix} + \begin{bmatrix} N_{0,H}(z) & N_{1,H}(z) \\ N_{0,V}(z) & N_{1,V}(z) \end{bmatrix}$$

Equation (1)

Normally the S/N ratio (also called the SN ratio, SNR, etc.) is used as an evaluation value indicating the noise in measured data, but under the present invention the ESNR is used as a more effective evaluation value of noise. In this Specification, the ESNR is indicated by $\gamma$ and defined by the equation below:

$$1/\gamma = 1/4(1/SNR_{s,0} + 1/SNR_{s,1} + 1/SNR_{r,0} + 1/SNR_{r,1})$$

Note that, in this equation, s and r represent the sample arm and reference arm of PS-OCT, respectively. 0 and 1 each represent the number of times, respectively.

The ESNR was introduced to indicate multiple independent SNRs using a single value. The subscripts 0, 1 represent measurement channels (refer to the optical detectors 22, 23 in FIG. 1). $SNR_{s,0}$, $SNR_{s,1}$, $SNR_{r,0}$ and $SNR_{r,1}$ having different combinations of subscripts represent the SNR that contributes from the sample arm to channel 0, SNR that contributes from the sample arm to channel 1, SNR that contributes from the reference arm to channel 0, and SNR that contributes from the reference arm to channel 1, respectively.

As shown in the second map from the top on the right side in FIG. 3, the retardation (phase delay amount, phase difference) measured by PS-OCT includes error and is distributed around the true value ($\pi/2$). Then, as the ESNR decreases, the margin of error increases, as shown in the top map on the right side in FIG. 3.

In addition, this phase difference distribution is not necessarily symmetrical, and may be asymmetrical with the true value not at the center, as is evident from the third and fourth maps from the top on the right side in FIG. 3.

In essence, as the retardation includes error and becomes noise, the phase difference distribution may not be normal or symmetrical around the true phase constant. In such cases, the correct retardation cannot be obtained from any standard phase analysis where the average is taken.

The program proposed by the present invention is a program that causes the computer 30 to function as a means for converting the image data measured by PS-OCT using a distribution conversion function obtained by analyzing the characteristics of noise via Monte Carlo simulation to remove the systematic error and estimate the true value otherwise buried in noise and thereby correct the PS-OCT image more clearly, while the system proposed by the present invention is a PS-OCT system installed with this program to perform the above correction.

Operating Principles:

The program proposed by the present invention causes the computer 30 to function as a means for correcting the measured retardation distribution (phase difference distribution) based on the image data measured by PS-OCT to obtain the true phase constant $\delta_T$ (true retardation value), and the operating principles (algorithms) of how this works is explained below.

Under the present invention, measured phase constant $\delta_M$ based on image data measured by PS-OCT is converted to symmetrical phase difference distribution $\delta_E$ using a non-linear function f. In essence, the symmetrical phase difference distribution $\delta_E$ is expressed as a power function of the measured phase constant $\delta_M$, or $\delta_E = f(\delta_M)$. In this Specification, this function is referred to as "conversion function" and expressed by Equation (2) below. This equation means that non-linear mapping is performed to convert the asymmetrical distribution $\delta_M$ of measured values to a distribution $\delta_E$ having the correct value as the center of weighting.

[Number 2]

$$\delta_E = \sum_{i=0}^{n} b_i(\gamma)\delta_M^i = b_0(\gamma) + b_1(\gamma)\delta_M + b_2(\gamma)\delta_M^2 + \ldots + b_n(\gamma)\delta_M^n \quad \text{Equation (2)}$$

In this Equation (2), bi represents a coefficient of conversion function. An optimal coefficient of conversion function bi (where i takes the value of 0, 1, 2, ..., n) is a function of ESNR$\gamma$, which should be determined by solving the simultaneous equations or using the least square method, as explained below, to create a table of bi ($\gamma$) beforehand.

For this purpose, the phase value is varied from 0 to $\pi$ in $\pi/m$ steps to obtain $\delta_M$ using the Monte Carlo method. The coefficient bi is determined by solving the simultaneous equations shown in Equation (3). In Equation (3), $<\delta_{M,\pi/m}>$ indicates a simulated value of retardation $\delta_M$ from 0 to $\pi$, based on simulation performed in $\pi/m$ steps, such as $\pi/60$ steps. Here, m takes the value of 1, 2, ..., 60, for example. Note that $<>$ in Equation (3) indicates that the value inside is an average of many values obtained by Monte Carlo simulation. To be specific, Equation (3) is rephrased as a matrix, as shown in Equation (4), to obtain the coefficient bi ($\gamma$).

[Number 3]

$$\begin{cases} 0 = b_0(\gamma) + b_1(\gamma)\langle\delta_{M,0}\rangle + b_2(\gamma)\langle\delta_{M,0}^2\rangle + \ldots + b_n(\gamma)\langle\delta_{M,0}^n\rangle \\ \frac{\pi}{m} = b_0(\gamma) + b_1(\gamma)\langle\delta_{M,\pi/m}\rangle + b_2(\gamma)\langle\delta_{M,\pi/m}^2\rangle + \ldots + b_n(\gamma)\langle\delta_{M,\pi/m}^n\rangle \\ \vdots \\ \pi = b_0(\gamma) + b_1(\gamma)\langle\delta_{M,\pi}\rangle + b_2(\gamma)\langle\delta_{M,\pi}^2\rangle + \ldots + b_n(\gamma)\langle\delta_{M,\pi}^n\rangle \end{cases} \quad \text{Equation (3)}$$

[Number 4]

$$D_T \simeq D_M \cdot B \quad \text{Equation (4)}$$

wherein:
$D_T = [0, \pi/1, \ldots, \pi/m, \ldots, \pi]^T$,
$B = [b_0(\gamma), \ldots, b_n(\gamma)]^T$, $$D_M = \begin{bmatrix} \langle\delta_{M,0}^0\rangle & \langle\delta_{M,0}^1\rangle & \ldots & \langle\delta_{M,0}^n\rangle \\ \vdots & \vdots & & \vdots \\ \langle\delta_{M,\pi/m}^0\rangle & \langle\delta_{M,\pi/m}^1\rangle & \ddots & \langle\delta_{M,\pi/m}^n\rangle \\ \vdots & \vdots & & \vdots \\ \langle\delta_{M,\pi}^0\rangle & \langle\delta_{M,\pi}^1\rangle & \ldots & \langle\delta_{M,\pi}^n\rangle \end{bmatrix}$$

Then, to determine the coefficient, a pseudo-inverse matrix DM+ of the n×m matrix DM of $\delta_{M,\pi/m}^n$ obtained by the simulation per Equation (4) is calculated numerically and Equation (5) below is calculated accordingly to obtain the coefficient. Note that $<>$ in Equation (4) indicates that the value inside is an average of many values obtained by Monte Carlo simulation.

[Number 5]

$$B = D_M^+ \cdot D_T \quad \text{Equation (5)}$$

The means for determining the coefficient using the least square method can also be employed, where the calculus of variation is used to uniquely determine an optimal coefficient of conversion function bi ($\gamma$), per the Monte Carlo method, so that the square error $R^2$ in Equation (6) below becomes the smallest. Here, too, the phase value is varied from 0 to $\pi$ in $\pi/m$ steps, such as $\pi/60$ steps where m=60, to obtain the simulated value $\delta_M$ using the Monte Carlo method. k indicates the number of phase measurements in fine steps and takes the value of 0, 1, 2, ..., m, such as m=60, for example.

[Number 6]

$$R^2 = \sum_{k=0}^{m} \left[\delta_{T,k} - \begin{pmatrix} b_0(\gamma) + b_1(\gamma)\langle\delta_{M,k}\rangle + \\ b_2(\gamma)\langle\delta_{M,k}^2\rangle + \ldots + b_n(\gamma)\langle\delta_{M,k}^n\rangle \end{pmatrix}\right]^2 \quad \text{Equation (6)}$$

Once an optimal coefficient of conversion function bi is determined, the conversion function $\delta_E = f(\delta_M)$ representing the symmetrical phase difference distribution $\delta_E$ is determined, where assigning the phase constant $\delta_M$ measured by PS-OCT gives $\delta_E$.

Then, by taking the average of $\delta_E$ as shown in Equation (7) below ($<>$ in Equation (7) means that the value is an average), the true phase constant $\delta_T$ can be obtained. Averaging is implemented based on the number of measurements performed to obtain one phase constant.

[Number 7]

$$\delta_T = \langle\delta_M\rangle \quad \text{Equation (7)}$$

Configuration:

The above explained the operating principles of the present invention, and in the PS-OCT system proposed by the present invention, the program proposed by the present invention causes the computer 30 used as an image processing device to function as the means described below according to these operating principles.

(1) Means for Creating Phase Difference Distributions

The means for creating phase difference distributions is to use simulation to create multiple phase difference distributions regarding retardation, as shown on the left side in FIG. 3, beforehand.

To be specific, multiple sets of phase difference distributions are created by changing the ESNR, where one set comprises 61 data sets (61 phase difference distributions) derived by dividing the horizontal axis by $\pi/m$, such as $\pi/60$ where m=60. Once created, these multiple sets of data are stored in the storage device 34.

(2) Means for Determining the Coefficient of Conversion Function

The means for determining the coefficient of conversion function is to determine the coefficient of conversion function bi for each of the multiple phase difference distribution sets.

As mentioned above, this coefficient of conversion function bi is determined by solving the simultaneous equations in Equation (3) or using the least square method per Equation (6). Once bi is determined, its table is created. This table of coefficient of conversion function bi is stored in the storage device 34.

(3) Means for Selecting the Phase Difference Distribution

The means for selecting the phase difference distribution is to, prior to correcting the phase difference distribution and phase constant of images measured by PS-OCT, estimate the value of ESNR from the measured data, system design, etc., and thereby determine which of the multiple phase difference distribution sets in (1) above (such as the phase difference distributions shown on the left side in FIG. 3) will be used.

(4) Means for Converting the Phase Difference Distribution Using the Conversion Function The means for calculating the conversion function is to use the coefficient bi corresponding to the phase difference distribution set selected by the selection means or the table thereof, from among the coefficients of conversion function bi or tables thereof as stored in the storage device 34, to assign a proper value to bi in Equation (2) and thereby obtain the conversion function $\delta_E = f(\delta_M)$ representing the symmetrical phase difference distribution from the retardation phase constant $\delta_M$ measured by PS-OCT.

(5) Means for Calculating the True Phase Constant

The means for calculating the true phase constant is to take the average of $\delta_E = f(\delta_M)$ representing the symmetrical phase difference distribution obtained as above, based on Equation (7) presented earlier, to calculate the true phase constant $\delta_T$.

TEST EXAMPLE 1

The inventors of the present invention conducted a comparison test of comparing simulated and measured values, in order to evaluate the program proposed by the present invention and the PS-OCT system installed with the program. In this comparison test, a sheet of glass, ⅛ wavelength plate, and ¼ wavelength plate were used as the samples (measuring targets), where the true values of retardation generated were 0, π/2 and π, respectively.

Note that, as mentioned above, the simulated value was obtained by determining the bi coefficient via Monte Carlo simulation beforehand and then using the obtained coefficient to convert the simulated data. The measured value was obtained by converting the measured data using the above coefficient. Monte Carlo simulation does not give a complete match, partly because this simulation includes random noise, and partly because bi is terminated after a finite number of terms.

In this test, a 1.3-µm probe was used for measurement by PS-OCT. With this PS-OCT, depth analysis in air was performed at 8.3 µm at a measurement speed of 30,000 lines per second. During measurement, the ESNR was changed by placing in front of the sample a non-polarization filter whose light intensity could be changed.

Figure 4:
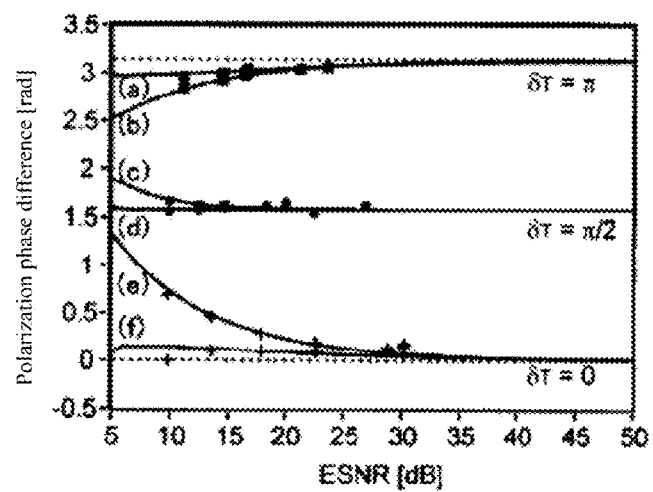
FIG. 4 is a graph showing the comparison test results of Test Example 1 pertaining to the present invention in which simulated and measured values were compared

FIG. 4 shows the comparison test results of simulations and tests. The dotted lines indicate the true retardation values (0, π/2, and π). The solid lines (b), (c) and (e) represent simple averages of measured retardation values without applying the correction under the present invention. The solid lines (a), (d) and (f) represent the simulated results according to the present invention, where the number of simulations performed to create coefficients was 65536, which also represents the number of data sets used to obtain coefficients and number of phase data sets used to produce results.

The ●, ■ and + marks positioned around the solid lines (b), (c) and (e) and (a), (d) and (f) represent the measured retardation values obtained by the test, and corrected test values obtained by correcting the measured values according to the present invention, respectively, and 64 measured data sets were used here. The simulated values and corrected test values roughly agree with one another in terms of the absolute value, ESNR dependence, etc.

TEST EXAMPLE 2

To evaluate the present invention, the inventors conducted a comparison test in which chicken breast meat (ex-vivo) normally used for PS-OCT evaluation was measured as a sample.

In this test, a 10-mm part of the sample was put through scan B comprising 512 of lines A. In other words, 512 lines A, obtained by measuring in the direction of A (depth direction), were obtained by scan B (scanning in the direction of B orthogonal to the direction of A). In addition, this measurement was performed 128 times at the same location of the sample. ESNRs smaller than 8 db were considered unstable and thus eliminated.

Figure 5:
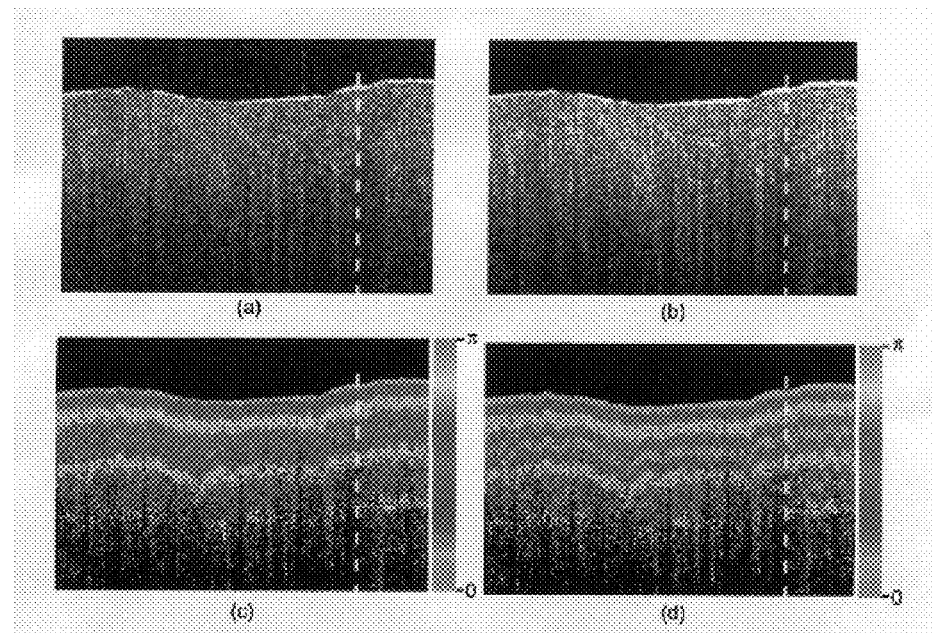
FIG. 5 shows images showing the test results of Test Example 2 pertaining to the present invention

FIG. 5 shows images illustrating the test results of Test Example 2. FIG. 5 (a) is an image of OCT intensity, FIG. 5 (b) is an image showing the value of ESNR in Paragraph 0064 by the image density, FIG. 5 (c) is an image of simple average phase, and FIG. 5 (d) is an image optimized by the correction according to the present invention.

Based on the results, the contrast dropped in the image of simple average phase in FIG. 5 (c), but not so much in FIG. 5 (d), in deep parts of the sample.

Figure 6:
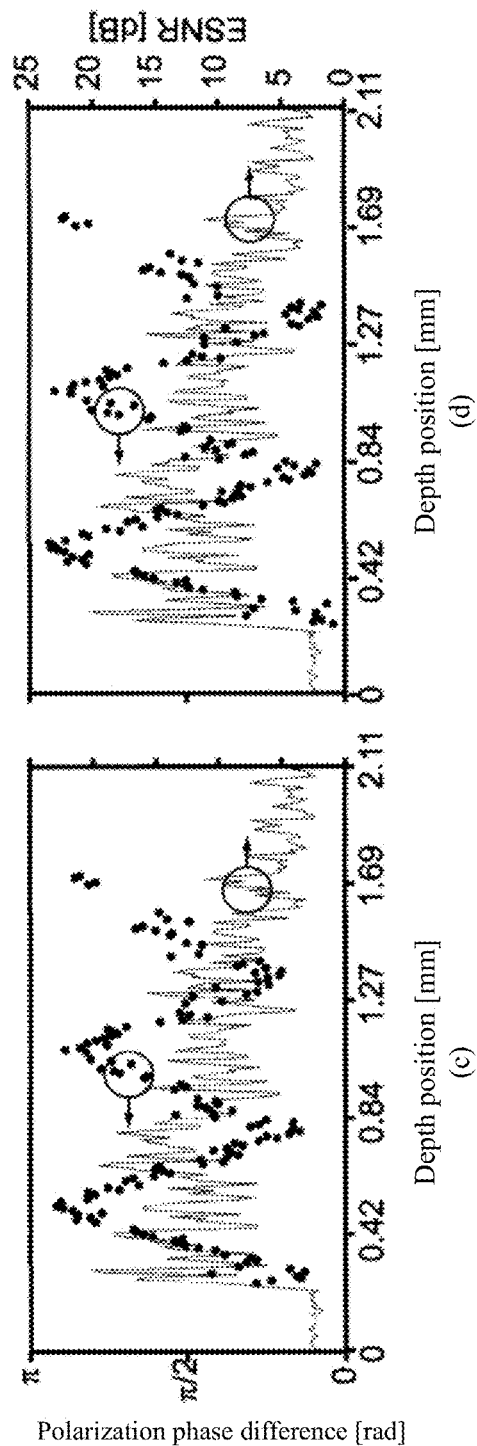
FIG. 6 shows images showing the sections cut along the dotted lines in FIG. 5 (c), (d)

FIG. 6 shows images of the sections cut along the dotted lines in FIG. 5 (c), (d), where the fine line represents the value of ESNR, while the thick dotted line represents the retardation. In FIG. 5 (c), (d), the value of ESNR (thin line) decreases toward the back (in deeper parts) of the sample, which suggests, in essence, decrease in signal intensity and increase in noise.

As for retardation, the retardation according to the present invention as shown in FIG. 6 (d) is clearer than the retardation obtained as a simple average as shown in FIG. 6 (c). Particularly in FIG. 6 (d), values near 0 and π are reproduced. This shows that the present invention is useful in image analysis based on PS-OCT.

In addition, while phase data near 0 and π are missing and continuity of phase change is lost in the processing without conversion (refer to FIG. 5 (c)), the processing results according to the present invention (refer to FIG. 5 (d)) show that phases near 0 and π are reproduced and the absolute value of retardation in the depth direction is correctly measured.

TEST EXAMPLE 3

To evaluate the present invention, the inventors measured the human eyeground (in-vivo) using PS-OCT. This measurement was performed using 1.0-µm probe beam at the depth of the eyeground of 11.0 µm, based on PS-OCT where the measurement speed was 30,000 lines per second.

Figure 7:
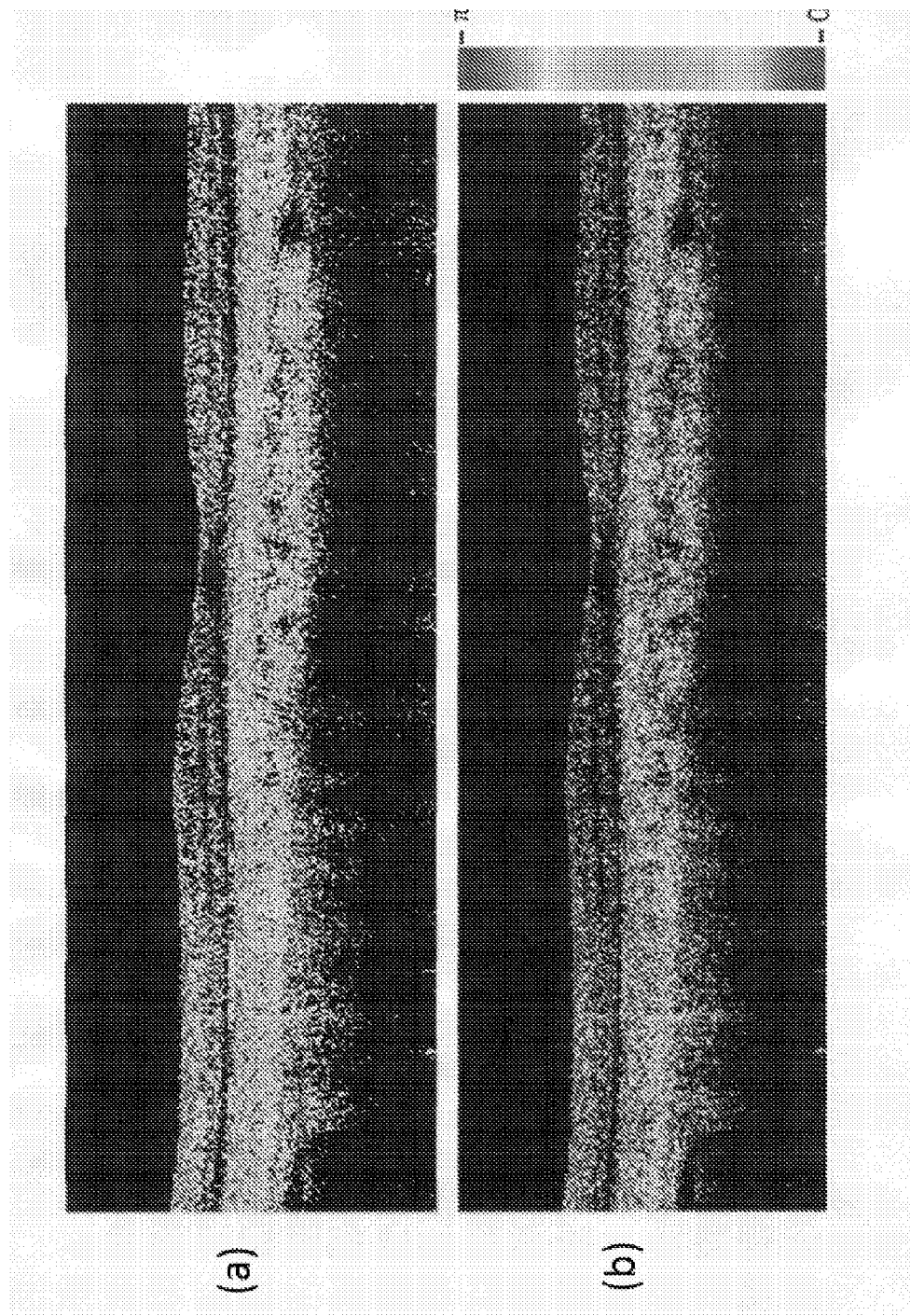
FIG. 7 shows images showing the test results of Test Example 3 pertaining to the present invention
Figure 8:
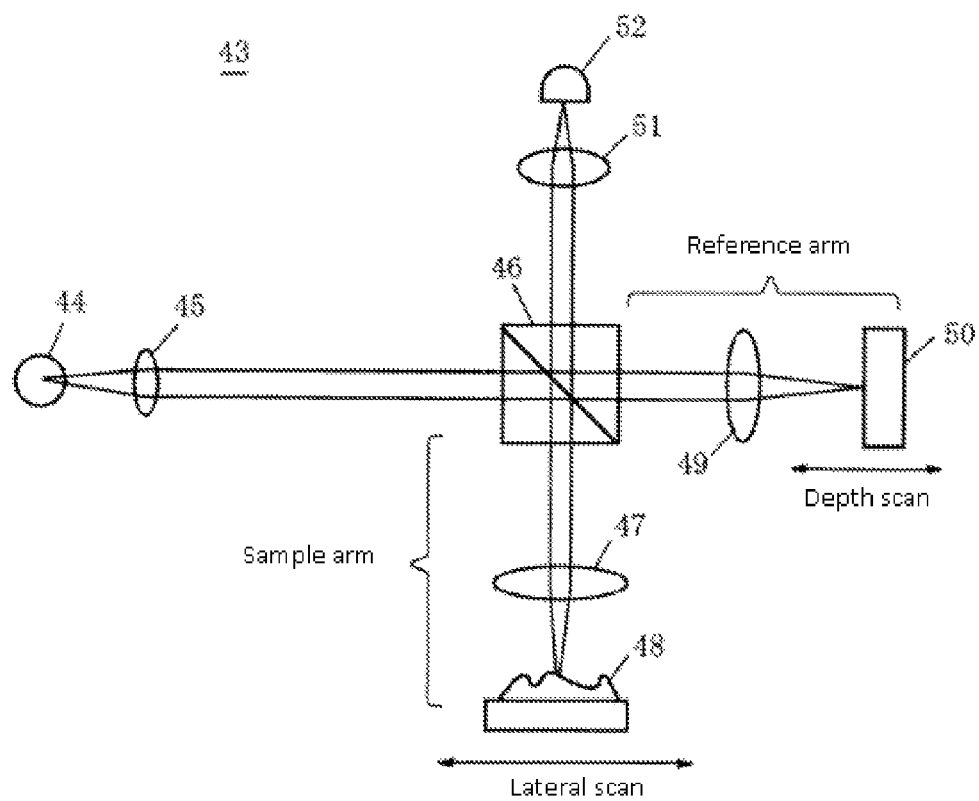
FIG. 8 is a diagram explaining the conventional OCT

FIG. 7 shows the images obtained by this test. FIG. 7 (a) is an image based on the conventional simple average processing, while FIG. 7 (b) is an image to which the correction processing per the present invention was applied.

Based on FIG. 7 (b), it seems the present invention allows the phase constant to be accurately reproduced near 0 representing the surface, and gives phase constants and phase difference distributions closer to the truth.

The above explained modes for carrying out the program proposed by the present invention and PS-OCT system installed with the program, but the present invention is not at all limited to these embodiments and it goes without saying that various embodiments are available to the extent allowed by the technical aspects specified in "What Is Claimed Is."

INDUSTRIAL FIELD OF APPLICATION

Traditionally PS-OCT was used in limited applications involving morphological observation of lesions, but the program proposed by the present invention and PS-OCT system installed with the program can be utilized, because of their configuration described above, as a useful means for computer diagnosis that permits accurate quantitative diagnosis, including diagnosis of disease stage of lesions, in clinical fields where broad, non-invasive tissue discrimination is required, such as ophthalmology, circulatory medicine, respiratory medicine, and digestive medicine, among others.

For example, by incorporating the present invention into a PS-OCT device for the anterior of the eye, non-contact, non-invasive observation of surgical scars becomes possible after glaucoma surgery, which dramatically improves the efficiency of determining the course of opthalmological treatment.

DESCRIPTION OF THE SYMBOLS

1 PS-OCT (polarization-sensitive optical coherence tomography device)
2 Light source
3, 12 Polarizer
4 EO modulator (polarization modulator, electro-optical modulator)
5 Fiber coupler (optical coupler)
6 Reference arm
7 Sample arm
8 Spectroscope
9 Fiber
10, 15, 18 Polarization controller
11 Collimating lens
13 Condensing lens
14 Reference mirror (fixed mirror)
16 Galvano-mirror
17 Sample
19 Diffraction lattice
20 Fourier conversion lens
21 Polarization beam splitter
22, 23 Optical detector (line CCD camera)
24 Fixed mirror
30 Computer (image processing device)
31 Input part
32 Output part
33 CPU
34 Storage device
35 Data bus

What is claimed is:

1. A non-transitory computer readable medium storing a program to be installed in a computer for processing measured data obtained by polarization-sensitive optical coherence tomography (PS-OCT), said program characterized in that it causes the computer to function as:

a means for creating and storing multiple sets of phase difference distribution data for different effective signal-to-noise ratios (ESNRs) beforehand, where each set comprises a distribution corresponding to each of multiple phase constants from 0 to $\pi$;

a means for determining a coefficient of non-linear conversion function for converting phase difference distribution data measured by PS-OCT to symmetrical phase difference distribution data;

a means for estimating an ESNR from phase difference distribution data measured by PS-OCT and then using the estimated ESNR to select one of the multiple sets of phase difference distributions created for different ESNRs;

a means for converting phase difference distribution data measured by PS-OCT to symmetrical phase difference distribution data, by using the conversion function based on the coefficient determined according to the selected set of phase difference distribution; and a means for obtaining a true phase constant by averaging the symmetrical phase difference distribution data, wherein the non-linear conversion function conforms to Equation (2) below;

where, in Equation (2), $\delta E$ is a symmetrical phase difference distribution, $\delta M$ is a phase constant measured by PS-OCT, bi (i=0, 1, 2, 3, . . . , n) is a coefficient of conversion function, and $\gamma$ is an ESNR, $$\delta_E = \sum_{i=0}^{n} b_i(\gamma)\delta_M^i = b_0(\gamma) + b_1(\gamma)\delta_M + b_2(\gamma)\delta_M^2 + \ldots + b_n(\gamma)\delta_M^n \quad \text{Equation (2)}$$

wherein $\gamma$ is defined as follows:

$$1/\gamma = 1/4(1/SNR_{S,0} + 1/SNR_{S,1} + 1/SNR_{r,0} + 1/SNR_{r,1})$$

wherein s and r represent a sample arm and reference arm of PS-OCT, respectively, and 0 and 1 each represent the number of times, respectively.

2. A non-transitory computer readable medium storing a program according to claim 1, characterized in that the means for determining the conversion function comprises creating Equation (3) as simultaneous equations of m+1 below with respect to the non-linear conversion function, over a range of 0 to $\pi$ as divided in $\pi/m$ steps, and then solving the simultaneous equations to create a table of the coefficient of conversion function bi;

where, in Equation (3), m represents a number of times $\pi$ is divided:

$$\begin{cases} 0 = b_0(\gamma) + b_1(\gamma)\langle\delta_{M,0}\rangle + b_2(\gamma)\langle\delta_{M,0}^2\rangle + \ldots + b_n(\gamma)\langle\delta_{M,0}^n\rangle \\ \frac{\pi}{m} = b_0(\gamma) + b_1(\gamma)\langle\delta_{M,\pi/m}\rangle + b_2(\gamma)\langle\delta_{M,\pi/m}^2\rangle + \ldots + b_n(\gamma)\langle\delta_{M,\pi/m}^n\rangle \\ \vdots \\ \pi = b_0(\gamma) + b_1(\gamma)\langle\delta_{M,\pi}\rangle + b_2(\gamma)\langle\delta_{M,\pi}^2\rangle + \ldots + b_n(\gamma)\langle\delta_{M,\pi}^n\rangle. \end{cases} \quad \text{Equation (3)}$$

3. A non-transitory computer readable medium storing a program according to claim 2, characterized in that the means for solving the simultaneous equations to determine the coefficient of conversion function comprises numerically obtaining a pseudo-inverse matrix DM+ of matrix DM per Equation (4) and then calculating Equation (5) to uniquely determine an optimal coefficient of conversion function bi; where, in Equation (4), m represents a number of times π is divided:

$$D_T \simeq D_M \cdot B \quad \text{Equation (4)}$$

wherein $$D_T = [0, \pi/1, \ldots, \pi/m, \ldots, \pi]^T,$$

$$B = [b_0(\gamma), \ldots, b_n(\gamma)]^T,$$

$$D_M = \begin{bmatrix} \langle \delta_{M,0}^0 \rangle & \langle \delta_{M,0}^1 \rangle & \ldots & \langle \delta_{M,0}^n \rangle \\ \vdots & \vdots & & \vdots \\ \langle \delta_{M,\pi/m}^0 \rangle & \langle \delta_{M,\pi/m}^1 \rangle & \ddots & \langle \delta_{M,\pi/m}^n \rangle \\ \vdots & \vdots & & \vdots \\ \langle \delta_{M,\pi}^0 \rangle & \langle \delta_{M,\pi}^1 \rangle & \ldots & \langle \delta_{M,\pi}^n \rangle \end{bmatrix}$$

$$B \equiv D_M^+ \cdot D_T. \quad \text{Equation (5)}$$

4. A non-transitory computer readable medium storing a program according to claim 1, characterized in that the means for determining the coefficient of conversion function comprises using a calculus of variation to uniquely determine an optimal coefficient of conversion function bi in such a way as to minimize a square error indicated by Equation (6) below;
where, in Equation (6), m represents a number of times π is divided:

$$R^2 = \sum_{k=0}^{m} \left[ \delta_{T,k} - \left( \begin{array}{c} b_0(\gamma) + b_1(\gamma)\langle \delta_{M,k} \rangle + \\ b_2(\gamma)\langle \delta_{M,k}^2 \rangle + \ldots + b_n(\gamma)\langle \delta_{M,k}^n \rangle \end{array} \right) \right]^2. \quad \text{Equation (6)}$$

5. A polarization-sensitive optical coherence tomography (PS-OCT) system equipped with PS-OCT and a computer for processing measured data obtained by the PS-OCT,
said PS-OCT system characterized in that the computer has an input device, output device, CPU, and storage device and functions as:
a means for creating and storing multiple sets of phase difference distribution data for different ESNRs beforehand, where each set comprises a distribution corresponding to each of multiple phase constants from 0 to π;
a means for determining a coefficient of non-linear conversion function for converting phase difference distribution data measured by PS-OCT to symmetrical phase difference distribution data;
a means for estimating an effective signal-to-noise ratio (ESNR) from phase difference distribution data measured by PS-OCT and then using the estimated ESNR to select one of the multiple sets of phase difference distributions created for different ESNRs;
a means for converting phase difference distribution data measured by PS-OCT to symmetrical phase difference distribution data, by using the conversion function based on the coefficient determined according to the selected set of phase difference distribution; and
a means for obtaining a true phase constant by averaging the symmetrical phase difference distribution data, wherein the non-linear conversion function conforms to Equation (2) below;

where, in Equation (2), δE is a symmetrical phase difference distribution, δM is a phase constant measured by PS-OCT, bi (i=0, 1, 2, 3, . . . , n) is a coefficient of conversion function, and γ is an ESNR, $$\delta_E = \sum_{i=0}^{n} b_i(\gamma)\delta_M^i = b_0(\gamma) + b_1(\gamma)\delta_M + b_2(\gamma)\delta_M^2 + \ldots + b_n(\gamma)\delta_M^n \quad \text{Equation (2)}$$

wherein γ is defined as follows:

$$1/\gamma = 1/4(1/SNR_{S,0} + 1/SNR_{S,1} + 1/SNR_{r,0} + 1/SNR_{r,1})$$

wherein s and r represent a sample arm and reference arm of PS-OCT, respectively, and 0 and 1 each represent the number of times, respectively.

6. A PS-OCT system according to claim 5, characterized in that the means for determining the conversion function comprises creating Equation (3) as simultaneous equations of m+1 below with respect to the non-linear conversion function, over a range of 0 to π as divided in π/m steps, and then solving the simultaneous equations to create a table of the coefficient of conversion function bi;
where, in Equation (3), m represents a number of times π is divided:

$$\begin{cases} 0 = b_0(\gamma) + b_1(\gamma)\langle \delta_{M,0} \rangle + b_2(\gamma)\langle \delta_{M,0}^2 \rangle + \ldots + b_n(\gamma)\langle \delta_{M,0}^n \rangle \\ \frac{\pi}{m} = b_0(\gamma) + b_1(\gamma)\langle \delta_{M,\pi/m} \rangle + b_2(\gamma)\langle \delta_{M,\pi/m}^2 \rangle + \ldots + b_n(\gamma)\langle \delta_{M,\pi/m}^n \rangle \\ \vdots \\ \pi = b_0(\gamma) + b_1(\gamma)\langle \delta_{M,\pi} \rangle + b_2(\gamma)\langle \delta_{M,\pi}^2 \rangle + \ldots + b_n(\gamma)\langle \delta_{M,\pi}^n \rangle. \end{cases} \quad \text{Equation (3)}$$

7. A PS-OCT system according to claim 6, characterized in that the means for solving the simultaneous equations to determine the coefficient of conversion function comprises numerically obtaining a pseudo-inverse matrix DM+ of matrix DM per Equation (4) and then calculating Equation (5) to uniquely determine an optimal coefficient of conversion function bi;
where, in Equation (4), m represents a number of times π is divided:

$$D_T \simeq D_M \cdot B \quad \text{Equation (4)}$$

wherein $$D_T = [0, \pi/1, \ldots, \pi/m, \ldots, \pi]^T,$$

$$B = [b_0(\gamma), \ldots, b_n(\gamma)]^T,$$

$$D_M = \begin{bmatrix} \langle \delta_{M,0}^0 \rangle & \langle \delta_{M,0}^1 \rangle & \ldots & \langle \delta_{M,0}^n \rangle \\ \vdots & \vdots & & \vdots \\ \langle \delta_{M,\pi/m}^0 \rangle & \langle \delta_{M,\pi/m}^1 \rangle & \ddots & \langle \delta_{M,\pi/m}^n \rangle \\ \vdots & \vdots & & \vdots \\ \langle \delta_{M,\pi}^0 \rangle & \langle \delta_{M,\pi}^1 \rangle & \ldots & \langle \delta_{M,\pi}^n \rangle \end{bmatrix}$$

$$B \equiv D_M^+ \cdot D_T. \quad \text{Equation (5)}$$

8. A PS-OCT system according to claim 5, characterized in that the means for determining the coefficient of conversion function comprises using a calculus of variation to uniquely determine an optimal coefficient of conversion function bi in such a way as to minimize a square error indicated by Equation (6) below;

where, in Equation (6), m represents a number of times $\pi$ is divided:

$$R^2 = \sum_{k=0}^{m} \left[ \delta_{T,k} - \begin{pmatrix} b_0(\gamma) + b_1(\gamma)\langle\delta_{M,k}\rangle + \\ b_2(\gamma)\langle\delta_{M,k}^2\rangle + \ldots + b_n(\gamma)\langle\delta_{M,k}^n\rangle \end{pmatrix} \right]^2.$$

Equation (6)

\* \* \* \* \*